(12) United States Patent
Suzuki et al.

(10) Patent No.: US 8,932,323 B2
(45) Date of Patent: Jan. 13, 2015

(54) TREATMENT TOOL FOR ENDOSCOPE

(75) Inventors: Keita Suzuki, Tokyo (JP); Atsushi Ban, Tokyo (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 746 days.

(21) Appl. No.: 12/028,407

(22) Filed: Feb. 8, 2008

(65) Prior Publication Data

US 2008/0125809 A1 May 29, 2008

Related U.S. Application Data

(63) Continuation of application No. PCT/JP2005/014768, filed on Aug. 11, 2005.

(30) Foreign Application Priority Data

Feb. 13, 2004 (JP) ................. P2004-036601

(51) Int. Cl.
*A61B 17/00* (2006.01)
*A61B 10/06* (2006.01)
*A61B 17/128* (2006.01)
*A61B 1/018* (2006.01)
(Continued)

(52) U.S. Cl.
CPC .............. *A61B 10/06* (2013.01); *A61B 17/1285* (2013.01); *A61B 1/018* (2013.01); *A61B 17/3478* (2013.01); *A61B 2017/2931* (2013.01); *A61B 2217/005* (2013.01); *A61B 2217/007* (2013.01)
USPC .......................................... 606/205; 600/562

(58) Field of Classification Search
USPC .......................................... 606/205; 600/562
See application file for complete search history.

(56) References Cited

U.S. PATENT DOCUMENTS 4,919,152 A 4/1990 Ger
5,354,291 A * 10/1994 Bales et al. ..................... 604/35
(Continued)

FOREIGN PATENT DOCUMENTS

JP S52-33113 7/1977
JP H5-51314 7/1993
(Continued)

OTHER PUBLICATIONS

Japanese Office Action dated Nov. 4, 2009 with English Translation.
(Continued)

*Primary Examiner* — Max Hindenburg
*Assistant Examiner* — Renee Danega
(74) *Attorney, Agent, or Firm* — Scully, Scott, Murphy & Presser, P.C.

(57) ABSTRACT

An treatment tool for a endoscope comprises a treatment tool insertion portion to be inserted into a channel of the endoscope; an open/close member support portion formed in a distal end of the treatment tool insertion portion; an open/close member which is freely supported so as to be opened or closed and treats a target site; a liquid conduit which transports a liquid to a target site, liquid conduit being provided on an outside of the open/close member in a direction orthogonal to a lengthwise direction of the open/close member, and comprising at least one distal end aperture which opens toward the distal end direction of the open/close member support portion, the liquid conduit transports.

5 Claims, 11 Drawing Sheets

(51) Int. Cl.
 *A61B 17/34* (2006.01)
 *A61B 17/29* (2006.01)

(56) References Cited

U.S. PATENT DOCUMENTS

| | | | | |
|---|---|---|---|---|
| 5,373,854 A | * | 12/1994 | Kolozsi | 600/562 |
| 5,386,817 A | * | 2/1995 | Jones | 600/104 |
| 5,456,684 A | | 10/1995 | Schmidt et al. | |
| 6,059,719 A | * | 5/2000 | Yamamoto et al. | 600/127 |
| 6,066,102 A | | 5/2000 | Townsend et al. | |
| 6,394,964 B1 | * | 5/2002 | Sievert et al. | 600/564 |
| 2004/0267303 A1 | * | 12/2004 | Guenst | 606/205 |

FOREIGN PATENT DOCUMENTS

| | | |
|---|---|---|
| JP | H11-047135 | 2/1999 |
| JP | 11-342135 | 12/1999 |
| JP | 2001-327510 | 11/2001 |
| JP | 2001-327512 A | 11/2001 |
| JP | 2002-505904 A | 2/2002 |
| JP | 2004-275548 A | 10/2004 |
| JP | 2005-505904 A | 2/2005 |
| JP | 2005-224426 A | 8/2005 |
| WO | WO 99/45847 | 9/1999 |
| WO | WO 03/032415 A2 | 4/2003 |

OTHER PUBLICATIONS

Japanese Official Action dated Mar. 2, 2010 together with an English language translation.

Korean Office Action (Notice of Allowance) dated May 20, 2010 from corresponding Korean application No. 10-2008-7003037, together with an English language translation.

* cited by examiner

TREATMENT TOOL FOR ENDOSCOPE

CROSS-REFERENCE TO RELATED APPLICATIONS

This is a Continuation Application of International Application No. PCT/JP2005/014768, filed Aug. 11, 2005. This application is related to Japanese Patent Application No. 2004-036601 filed on Feb. 13, 2004. The contents of the aforementioned applications are incorporated herein by reference.

TECHNICAL FIELD

The present invention relates to a treatment tool for an endoscope used while being inserted in a channel of the endoscope.

BACKGROUND ART

Hemorrhaging occasionally occurs when accomplishing treatment with an endoscope in the mucous membrane of the inner wall of digestive organs and the like. In order to flush the hemorrhage, a treatment tool for an endoscope having a liquid conduit is occasionally used. When the treatment tool for the endoscope is forceps which is a set of treatment pieces attached by pins so as to freely open and close, in the installation spacer in the distal end of a flexible sheath, a liquid conduit is arranged on the axis line of the flexible sheath. A liquid conduit passes between the two pins provided to each of the treatment pieces, and opens in the center of the front surface of the installation spacer. After opening the set of treatment pieces to start the transport of water, water is sprayed toward the front from between the treatment pieces.

Patent Document 1: Japanese Unexamined Patent Application, First Publication No. 2004-275548

DISCLOSURE OF THE INVENTION

Considering these circumstances, the present invention has the object of facilitating liquid transport irrespective of the open or close state of the distal end.

The present invention is an treatment tool for a endoscope characterized in that it comprises a treatment tool insertion portion to be inserted into a channel of the endoscope; an open/close member support portion formed in a distal end of the treatment tool insertion portion; an open/close member which is freely supported so as to be opened or closed and treats a target site; a liquid conduit which transports a liquid to a target site, liquid conduit being provided on an outside of the open/close member in a direction orthogonal to a lengthwise direction of the open/close member, and comprising at least one distal end aperture which opens toward the distal end direction of the open/close member support portion, the liquid conduit transports.

In addition, the present invention is characterized in that the distal end aperture of the liquid conduit is provided in a position which has shifted approximately 90 degrees around the axis line of the treatment tool insertion portion relative to an open/close direction of the open/close member.

Furthermore, the present invention is characterized in that the liquid conduit is provided on an outside of the treatment tool insertion portion.

Furthermore, the present invention is characterized in that the treatment tool for the endoscope is biopsy forceps, or high-frequency forceps, or a clip.

Furthermore the present invention is an treatment tool for a endoscope characterized in that it comprises a treatment tool insertion portion to be inserted into a channel of the endoscope; an open/close member support portion formed in a distal end of the treatment tool insertion portion; an open/close member which is freely supported so as to be opened or closed and treats a target site; a transmission member which is coupled to the open/close member passing through a hole formed in the open/close member support portion from the treatment tool insertion portion in order to transmit a driving force on the open/close member side; and a liquid transport flow path which is provided within the treatment tool insertion portion and transports a liquid to a target site, the liquid transport flow path having a flow path area larger than a flow path area formed between the hole and transmission member.

BEST MODE FOR CARRYING OUT THE INVENTION

An explanation of an embodiment of the invention is provided hereafter, with reference to the drawings.

First Embodiment

First, an explanation is provided regarding to a first embodiment, with reference to FIGS. 1 to 5. In the present embodiment, an example is described in which the treatment tool for the endoscope is high-frequency forceps.

Figure 1:
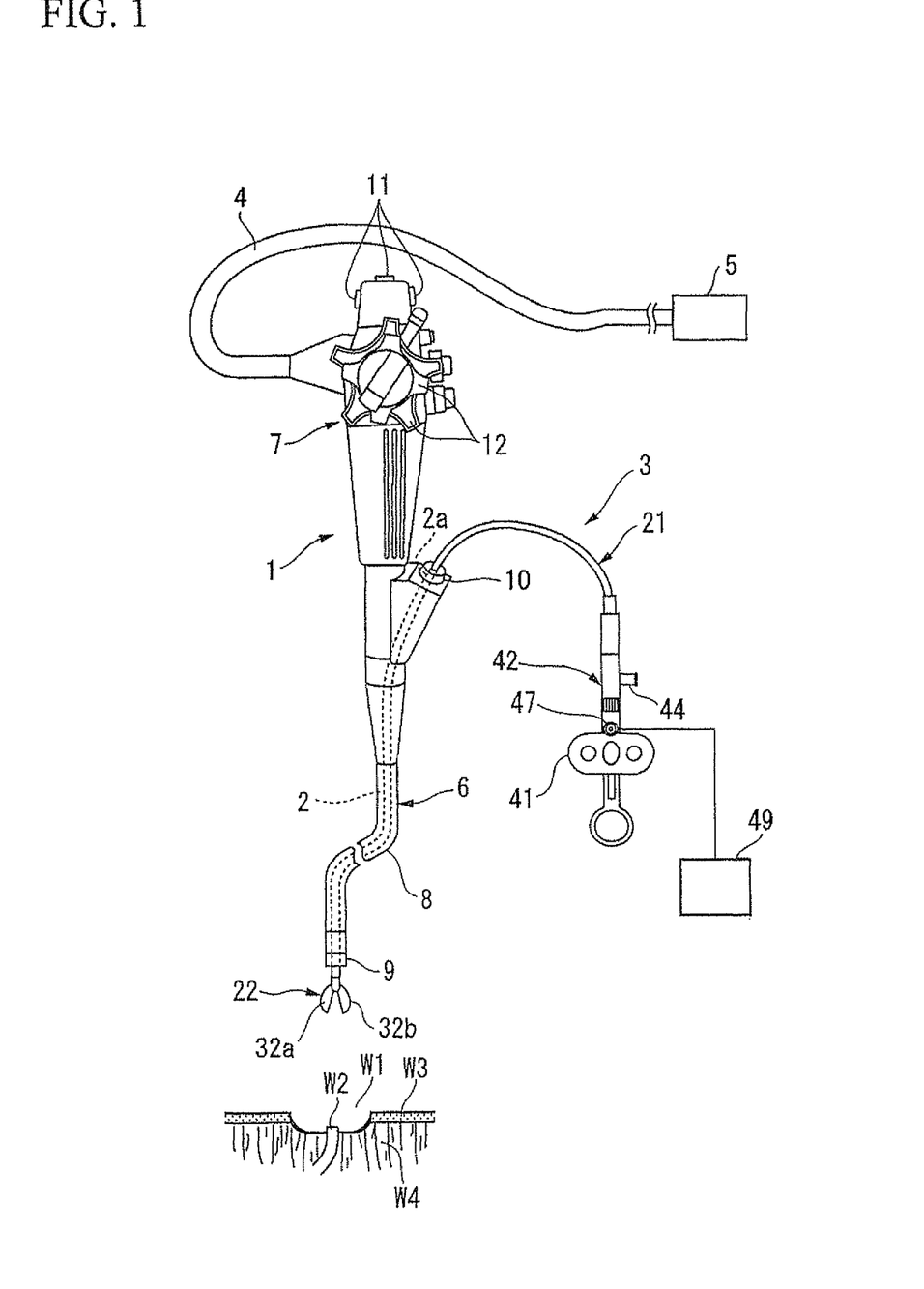
FIG. 1 is a diagram illustrating high-frequency forceps and an endoscope according to an embodiment of the present invention.

A schematic structure of an endoscope system which includes the treatment tool for the endoscope of the present embodiment is shown in FIG. 1. As shown in FIG. 1, the endoscope system comprises an endoscope 1, high-frequency forceps (treatment tool for endoscope) 3 inserted into the forceps channel 2 of the endoscope 1, and an endoscope body 5 connected via a universal code 4 to the endoscope 1.

The endoscope 1 comprises a flexible insertion portion 6 inserted into the living body, and an operation portion 7 connected to the proximal end (outside of the body) of the insertion portion 6, and the universal code 4.

To the distal end of the insertion portion 6 is connected a flexible bend portion 8, to the distal end of which is connected a distal end cover 9. In the distal end cover 9 is housed a photographic image unit, not shown in the drawing, for observing the inside of the body, and an illumination unit which provides illumination light. On the distal end surface of the distal end cover 9 is formed an aperture of the forceps channel 2. The forceps channel 2 comprises a forceps aperture 2a on the side of the operation portion 7, which communicates to the inside and outside of the body. To forceps aperture 2a is attached a forceps stopper 10.

The operation portion 7 comprises, other than the forceps aperture 2a, plural switches 11 and plural operation knobs 12. On the switches 11 is provided a switch to record an image photographed by the photographic unit, or a switch to change the illumination or the like. Signals of each switch is sent to the endoscope main body 5 via the universal cable. The operation knobs 12 include a knob for directing the flexible bend portion 8 to a certain direction.

The endoscope main body 5 is provided with a unit for processing or display of an image photographed by the endoscope 1, an illumination light source for photography, or the like.

As shown in FIGS. 2 to 5, the high-frequency forceps 3 are energy forceps that are capable of accomplishing hemostasis by burning the blood vessels W2, exposed by a cross section, the mucous membrane tissue W3 on the its periphery, or the submucosal layer tissue W4 and the like, made by an incision of the inner wall W1 of the digestive organs. The high-frequency forceps 3 comprise a treatment portion 22 provided in the distal end of the flexible treatment tool insertion portion 21 and two operation wires 23a and 23b (transmission member, see FIG. 3) which accomplish an open/close operation of the treatment portion 22, and a treatment tool operation portion 24 provided at the proximal end of a treatment tool insertion portion 21.

Figure 3:
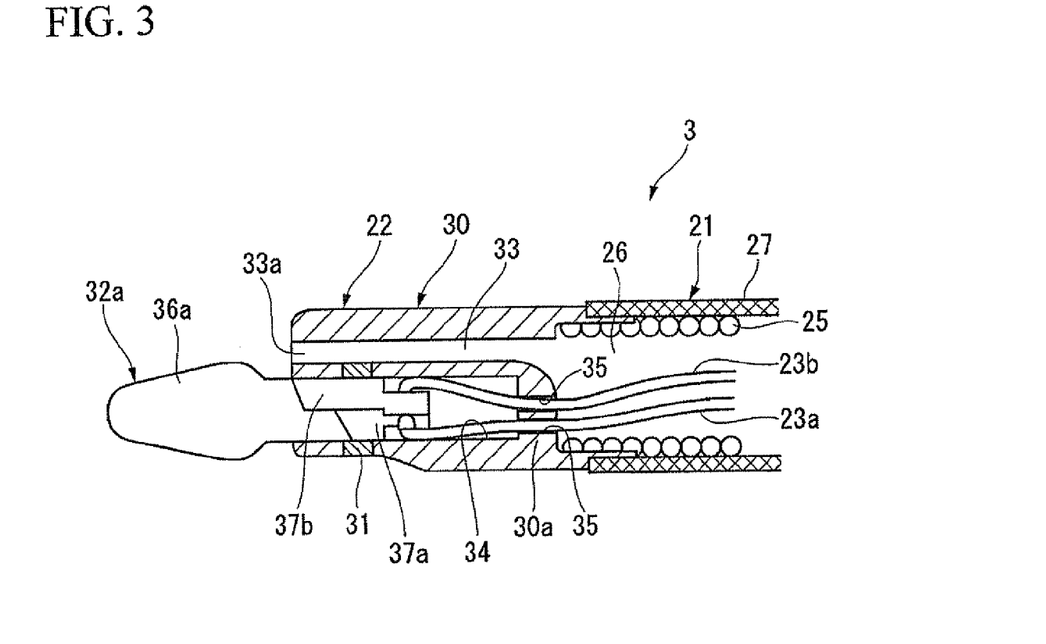
FIG. 3 is a cross-sectional view along the line III-III of FIG. 2.

As shown in FIG. 3, the treatment tool insertion portion 21 comprises an inner sheath in the form of a coil 25. Inside of the inner sheath 25 is formed a liquid conduit 26 in which liquid flows along the inner sheath 25. Within the liquid conduit 26 are inserted operation wires 23a and 23b. The outside of the inner sheath 25 is covered with a tube-like outer sheath 27 formed from an insulation member. By this means, the inner sheath 25 is insulated by the outer sheath 27 from its outside.

Figure 2:
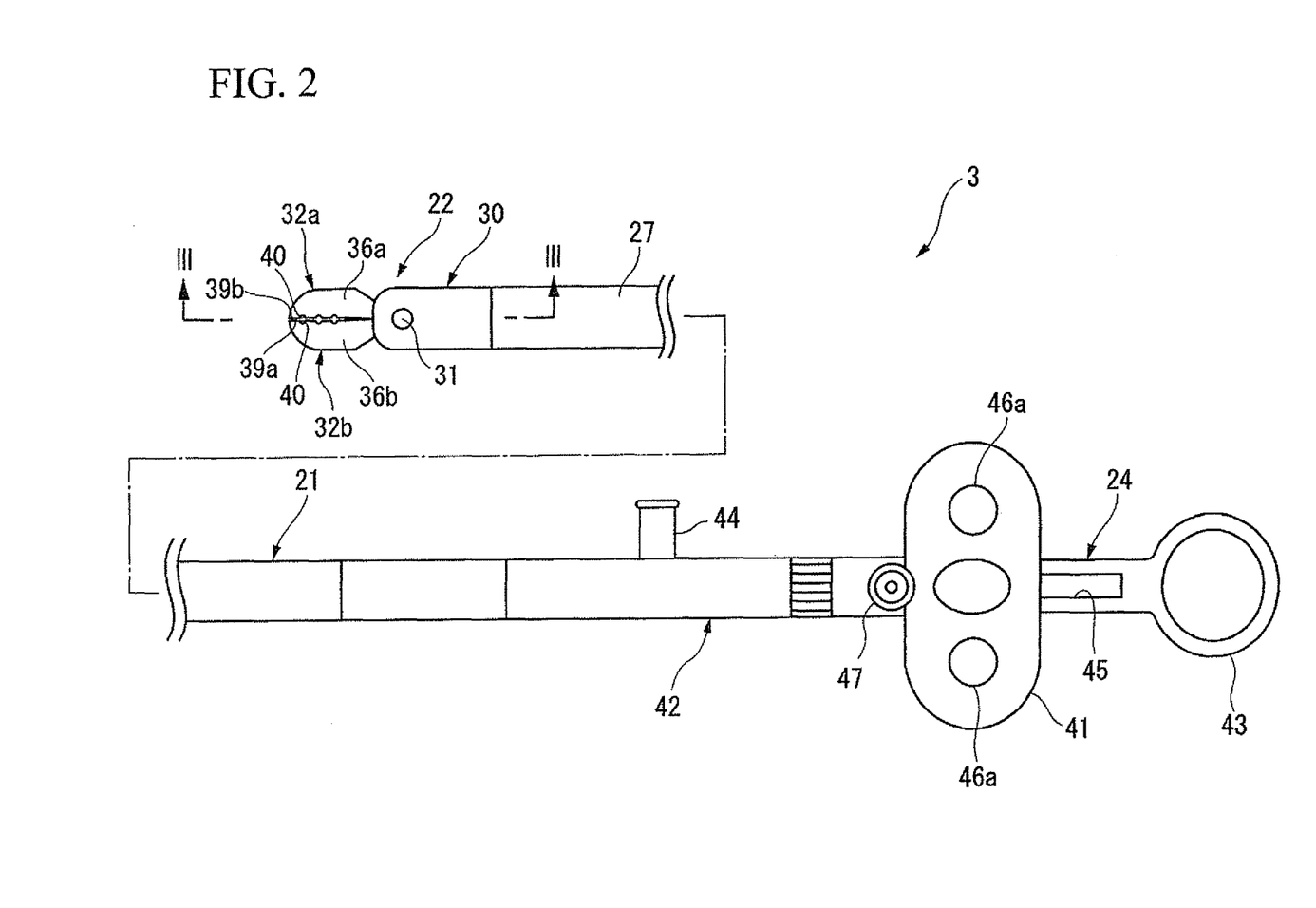
FIG. 2 is a diagram illustrating the structure of the high-frequency forceps.

As shown in FIG. 2 and FIG. 3, treatment portion 22 comprises a distal end cover (open/close member support portion) 30 secured to the distal end of the treatment tool insertion portion 21, and a set of forceps cups (open/close members) 32a and 32b, supported so as to freely rotate by the pin 31 of the cover 30.

The distal end cover 30 has an approximate cylindrical shape, and comprises a liquid transport lumen 33 which extends from the proximal end where it is attached to the treatment tool insertion portion 21 to the distal end which faces the hemorrhage site. The liquid transport lumen 33 is a liquid conduit which passes through along the lengthwise direction of the distal end cover 30. On the distal end surface of the distal end cover 30 is formed a distal end aperture 33a of the liquid transport lumen 33. A single distal end aperture 33a is arranged on the outside in the diameter direction orthogonal to the lengthwise direction of the forceps cups 32a and 32b, and the cover 30, which is open toward the tip (distal end).

In the distal end the cover 30, a slit 34 is provided in parallel to the liquid transport lumen 33. The slit 34 is a groove formed facing the proximal end side of the distal end the cover 30 from the distal end side of the distal end the cover 30. In the slit 34, two insertion through-holes 35 are provided in the wall 30a of the proximal end side of the distal end the cover 30, approximately parallel to the axis line of the distal end the cover 30. The insertion through-hole 35 communicates to the treatment tool insertion portion 21 and the slit 34. In the insertion through-hole 35, one of the operation wires 23a or 23b is inserted so as to be capable of advancing or retreating.

Each of the forceps cup 32a, 32b are arranged facing and along the slit 34 provided in the distal end the cover 30. The forceps cups 32a and 32b comprise cups 36a and 36b, and arms 37a and 37b extendingly extends from the proximal end of the cups 36a and 36b rearward (toward the treatment tool insertion portion 21 side).

Figure 5:
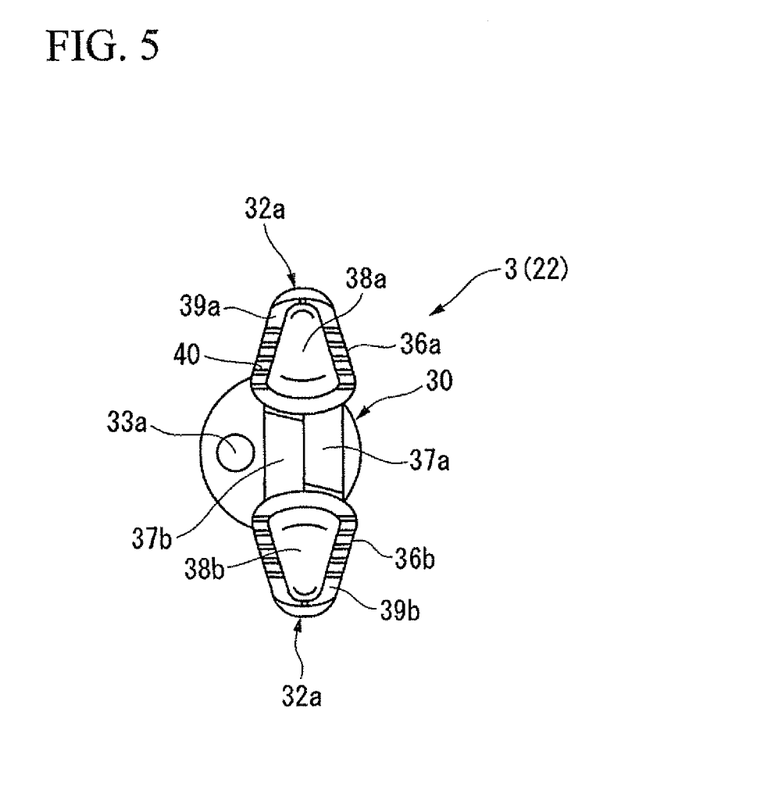
FIG. 5 is a diagram on Arrow A of FIG. 4.

As shown in FIG. 5, the cups 36a and 36b comprise indentations 38a and 38b on the surfaces facing each other. The forceps surface 39a which forms an outer periphery of the indentation 38a connects to another cup 36b, and plural grooves 40 are provided with a predetermined spacing. In the same manner, the forceps surface 39b which forms the outer periphery of the indentation 38b connects to another cup 36a, and plural grooves 40 are provided with a predetermined spacing.

Figure 4:
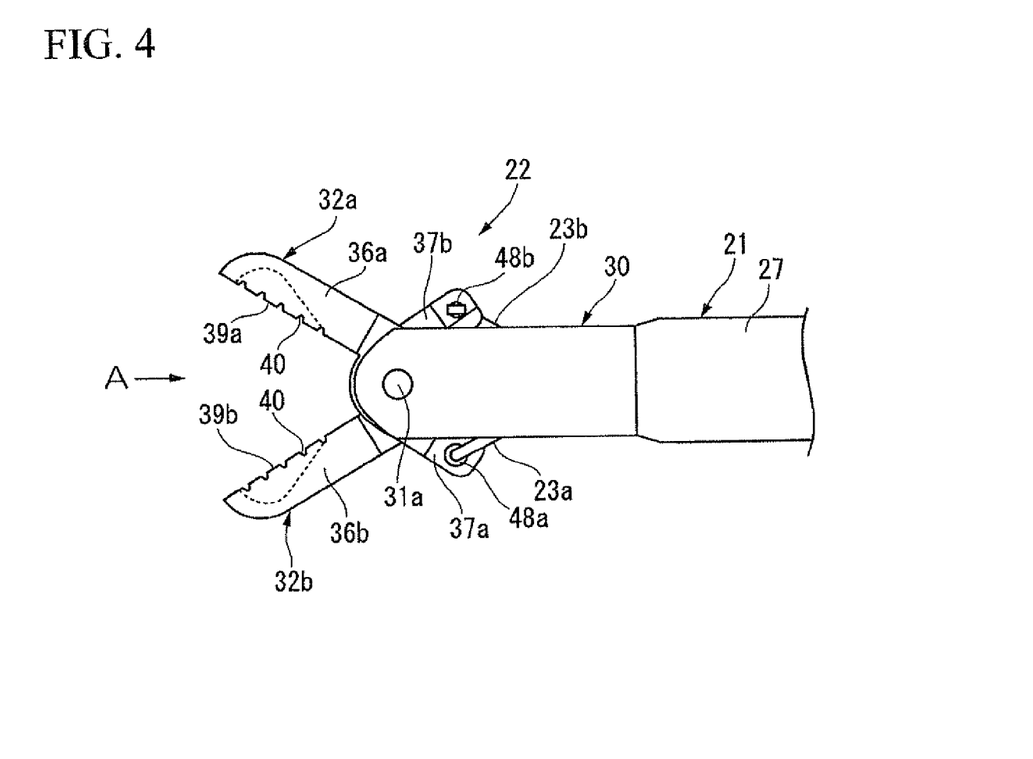
FIG. 4 is a diagram illustrating a set of energy forceps part of the high-frequency forceps in the open state.

As shown in FIG. 3 and FIG. 4, the arm 37a of forceps cup 32a extends rearward from the proximal end of the cup 36a. A hole 48a is formed in the rear portion of the arm 37a, and engages with the distal end of the operation wire 23a. The forceps cup 32a is rotatably supported by a pin 31 between the end of the arm 37a and the cup 36a. In the same manner, a hole 48b is formed in the rear portion of the arm 37b, and engages with the distal end of the operation wire 23b. The predetermined position of arm 37b is supported by the pin 31 (see FIG. 3) so as to freely rotate. The forceps cups 32a and 32b rotate about the pin 31. Each of the pins 31, the arms 37a and 37b, and each distal end of the operation wires 23a and 23b forms a link mechanism which opens and closes the set of the forceps cups 32a and 32b.

The distal ends of operation wire 23a and operation wire 23b respectively engage with forceps cup 32a and forceps cup 32b, passing through the insertion through-hole 35 of the distal end the cover 30. Each operation wire 23a and 23b is covered with a sheath having an insulating conductive material. The distal ends of the operation wires 23a and 23b are electrically connected to the forceps cups 32a and 32b. The proximal end of the operation wires 23a and 23b pass through the treatment tool insertion portion 21, and are drawn out to the treatment tool operation portion 24, and connected to the handle 41 of the treatment tool operation portion 24.

The treatment tool operation portion 24 comprises an operation component main body 42 and a slidable handle 41 relative to the operation component main body 42.

To the distal end of the operation component main body 42 is connected the proximal end of the treatment tool insertion portion 21. On the proximal end of the operation component main body 42 is provided a finger ring 43. In the distal end side of the operation component main body 42 is provided a lure cock 44. The inner passage of the lure cook 44 passes within the operation component main body 42 and communicates to a liquid conduit 26 (see FIG. 3). On the finger ring 43 side of the operation component main body 42 is formed a slide groove 45 along the lengthwise direction of the operation component main body 42. In slide groove 45 a handle 41 is inserted and mounted so as to be freely slidable. On the handle 41 are secured the operation wires 23a and 23b which pass through the operation component main body 42.

The handle 41 is provided with finger holes 46a and 46b on which the operator can place his fingers, and a terminal 47. The terminal 47 is electrically connected to the operation wires 23a and 23b. When a high-frequency electric power source 49 is connected to the terminal 47 (see FIG. 1), the electric power of which can be conducted to the set of the forceps cups 32a and 32b.

To the lure cock 44 can be attached a liquid supply device (not shown) in which a liquid is stored. As the liquid supply device, a syringe or a liquid pump may be used. As the liquid, water, physiological saline solution, a hemostat, or a stain solution and the like may be used.

An explanation of the operation of the high-frequency forceps 3 is provided next.

Initially, the high-frequency forceps 3 are inserted into the channel 2 of the endoscope 1, and the terminal 47 is connected to the high-frequency electric power source 49. The distal ends of the high-frequency forceps 3 are positioned in a close proximity to the periphery of the hemorrhage site (for example, the blood vessel W2 shown in FIG. 1). The insertion portion 6 of the endoscope 1 is bent so that the distal end side of the distal end the cover 30 of the high-frequency forceps 3 faces the hemorrhage site. The liquid in the lure cock 44 of the treatment tool operation portion is connected to a syringe in which a liquid is stored, and the liquid delivered from the syringe to the liquid conduit 26 is sprayed facing the hemorrhage site through the distal end aperture 33a from the liquid transport lumen 33 of the treatment unit 22, being led to the treatment unit 22 through a liquid conduit 26, flushing the blood on the periphery of the hemorrhage site. While confirming the hemorrhage site by means of the photographic unit of the endoscope 1, the handle 41 of the treatment tool operation portion 24 is slid, opening the set of the forceps cups 32a and 32b.

Specifically, by pressing the handle 41 in the distal end side, the operation wires 23a and 23b are advanced toward the site of the hemorrhage. When the operation wires 23a and 23b are advanced, the arms 37a and 37b supported by the pin 31 to the distal end the cover 30 move so as to be space apart in the direction approximately orthogonal to the lengthwise direction of the treatment units 22. Each of the forceps cups 32a and 32b rotate about the pin 31, increasing the distance between each of the forceps surfaces 39a and 39b.

After opening the distal ends of the set of the forceps cups 32a and 32b of the treatment unit 22, the entire frequency forceps 3 are advanced. When the distal ends of the forceps cups 32a and 32b make contact with the inner wall W1 of the digestive organs, the handle 41 of the treatment tool operation portion 24 is drawn back. The operation wires 23a and 23b are withdrawn, and the arms 37a and 37b are drawn closer The forceps cups 32a and 32b rotate about the pin 31, closing the set of the forceps cups 32a and 32b.

The set of the forceps cups 32a and 32b, along with the submucosal layer tissue W4 on the periphery of the exposed blood vessels W2, sandwich the blood vessels W2 with forceps surfaces 39a and 39b. The tips of the sections of the blood vessels W2 are fitted into the indentations 38a and 38b of the forceps cups 32a and 32b, and do not make contact with the forceps surfaces 39a and 39b.

When high-frequency electric current is applied from the high-frequency electric power source 49, the submucosal layer tissue W4 making contact with the forceps surfaces 39a and 39b is cauterized such that the blood vessels W2 are included therein.

According to this embodiment, since a liquid transport lumen 33 is provided in the treatment unit 22, liquid can be sprayed in a direction approximately parallel to the direction in which the set of forceps 32a and 32b extend from the liquid transport lumen. Accordingly, while the high-frequency forceps 3 are supported in a state in which they are inserted into the endoscope 1, liquid can be flushed on the periphery of the hemorrhage, the position of which can be accurately confirmed. Since the lengthwise direction of the liquid transport lumen and the direction in which the set of the forceps cups 32a and 32b extend are approximately parallel, the position of spraying the liquid can be identified, and hemostasis can be quickly and simply accomplished.

Since the liquid conduit 26 and the liquid transport lumen 33 are provided in the treatment tool insertion portion 21 of the high-frequency forceps 3 and the distal end the cover 30 as a unit, while washing the affected area using the liquid transport, or immediately after washing, hemostasis can be accomplished with radio waves, which facilitate the procedures. Since the liquid transport lumen 33 and the set of the forceps cups 32a and 32b are arranged in different positions, the structure of the device can be simplified.

Since the distal end aperture 33a is formed closer to the proximal end side than the cup portions 36a and 36b of the forceps cups 32a and 32b, the liquid transport lumen 33 does not interfere with opening and closing of the forceps cups 32a and 32b. There is also no narrowing of the field of vision.

The clearance (flow path area) at the time the operation wires 23a and 23b pass through the wall 30a of the distal end the cover 30 is sufficiently small compared to the flow path area of the liquid transport lumen 33. Accordingly, even if the insertion through-hole 35 of the operation wires 23a and 23b is not of watertight construction, leakage of the liquid can be prevented.

In a configuration in which the operation wire passes through the liquid conduit, if the hole in the forceps cup through which the operation wire is drawn is large, then there would be a leakage of liquid, with the problem that liquid cannot be sprayed from the liquid conduit in the required amount. However, the structure of this embodiment solves such problems, and liquid transport can be accomplished to the required position with simple construction.

Second Embodiment

Figure 6:
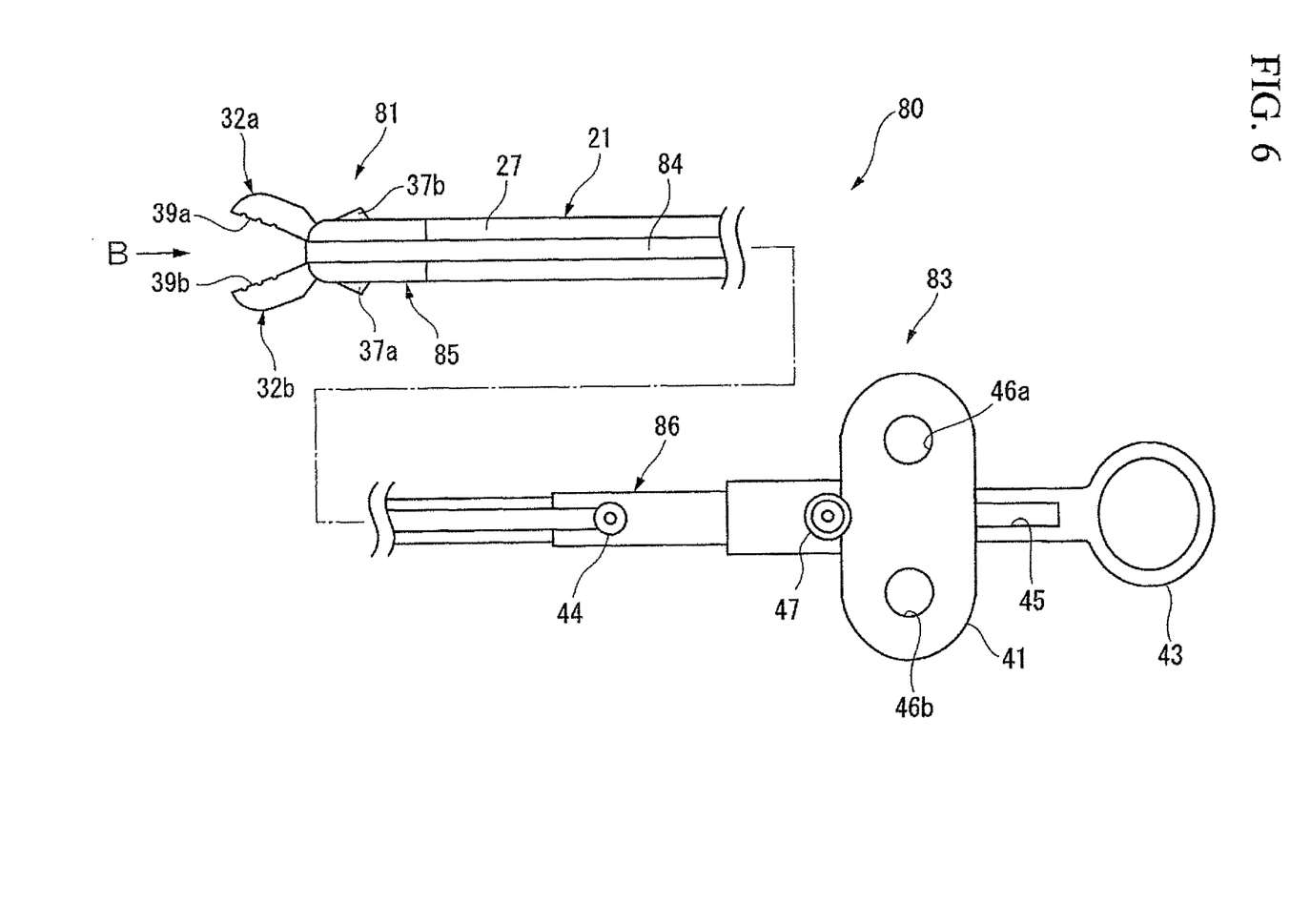
FIG. 6 is a diagram illustrating the structure of high-frequency forceps according to an embodiment of the present invention.
Figure 7:
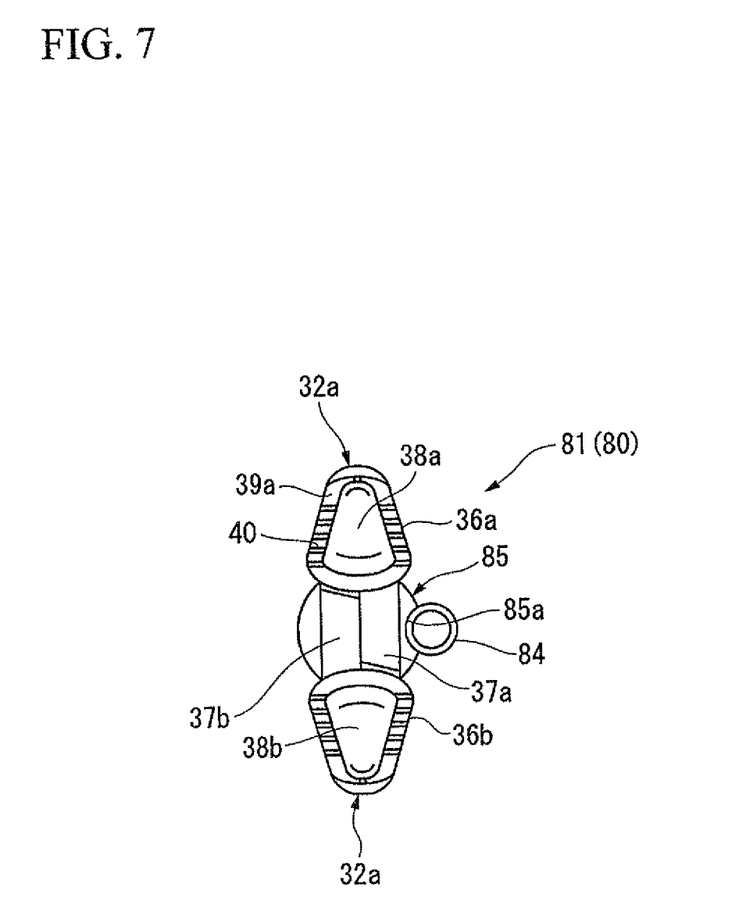
FIG. 7 is a diagram on Arrow B of FIG. 6.

First, an explanation is provided regarding to a second embodiment, with reference to FIG. 6 and FIG. 7. In the present embodiment, an example is provided in which the treatment tool for the endoscope is high-frequency forceps. Elements which are the same as those of the first embodiment are given the same symbols, and repetitive explanations are omitted.

As shown in FIG. 6 and FIG. 7, high-frequency forceps 80 are provided on a treatment unit 81 attached to the distal end of the flexible treatment tool insertion portion 21. To the proximal end of the treatment tool insertion portion 21 is attached a treatment tool operation portion 83. Along the treatment unit 81 and the treatment tool insertion portion 21 is arranged a liquid conduit 84 which transports sprayed liquid toward the site of the hemorrhage.

In the treatment unit 81, a set of the forceps cups 32a and 32b are supported so as to be freely rotated and face a distal end cover (open/close member support portion) 85. The forceps cups 32a and 32b have the same construction as that of the first embodiment. The treatment unit 81 is constructed so as to freely rotate about an unshown pin, by means of a link mechanism formed from the arms 37a and 37b and the operation wires 23a and 23b.

The operation wires 23a and 23b are secured to the handle 41 of the treatment tool operation portion 83, passing through the inside of the distal end cover 85 and the treatment tool insertion portion 21

As shown in FIG. 7, a part of the outer periphery of the distal end cover 85 is indented. The distal end of a liquid conduit 84 is secured to the indentation 85a. The indentation 85a is attached along the length of the distal end cover 85 in a position which is approximately orthogonal to the open/close direction of the distal end of the set of the forceps cups 32a and 32b. A single distal end aperture 84 is arranged on the outside in the diameter direction orthogonal to the lengthwise direction of the forceps cups 32a and 32b, and distal end cover 85, which is open toward the tip (distal end).

As shown in FIG. 6, liquid conduit 84 is flexible, at least the part secured to the outer surface of the external sheath 27. The proximal end of the liquid conduit 84 is secured to the operation main body 86 of the treatment tool operation portion 83. To the proximal end of the liquid conduit 84 is attached the lure cock 44 to which a syringe can be connected.

The outer surface of the operation portion main body 86 of the treatment tool operation portion 83 is secured to the liquid conduit 84. The operation portion main body 86 is directly connected to the liquid conduit 84 and the lure cock 44. Other construction is the same as that of the first embodiment.

The treatment unit 81 is used while being inserted in the channel 2 of the endoscope 1. When accomplishing hemostasis, the distal end of the distal end cover 85 is directed to the hemorrhage site side, and liquid is sent from a syringe. The liquid sent from the syringe is sprayed from the distal end of the liquid conduit 84, flushing the blood on the periphery of the hemorrhage. After confirming the site of the hemorrhage by means of the liquid transport, the operation wires 23a and 23b are advanced or withdrawn, and the hemorrhage site and its periphery is sandwiched between the set of the forceps cups 32a and 32b. High frequency current is applied from the high frequency electric power source 49, and the submucosal layer tissue W4 in contact with the forceps surfaces 39a and 39b are cauterized while the blood vessels W2 is included therein According to this embodiment, transportation of a liquid to the hemorrhage site and its periphery, and hemostasis can be quickly accomplished. In particular, since the liquid conduit 84 is arranged on the outside of the treatment unit 81 and the treatment tool insertion portion 21, liquid transport and hemostasis can be accomplished with simple construction. Other effects are the same as those of the first embodiment.
Third Embodiment First, an explanation is provided of a third embodiment, with reference to FIGS. 8 and 9. In the third embodiment, the treatment tool for the endoscope is biopsy forceps. The same symbols are applied to the same construction elements as those of the first embodiment. Explanations which are repetitive to those of the first embodiment are omitted.

Figure 8:
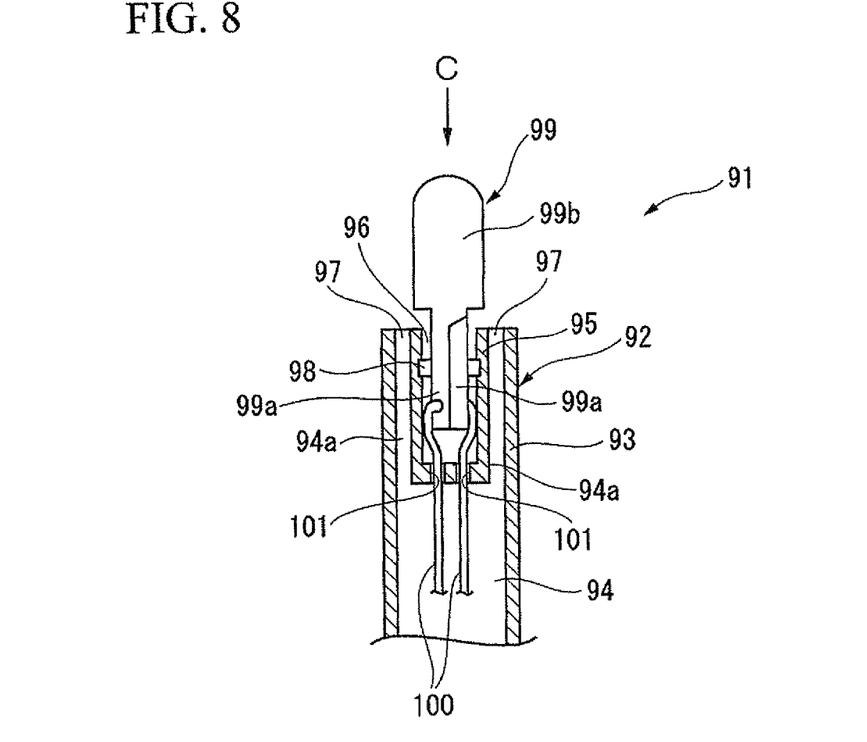
FIG. 8 is a cross-sectional view of the distal end portion of biopsy forceps according to an embodiment of the present invention.
Figure 9:
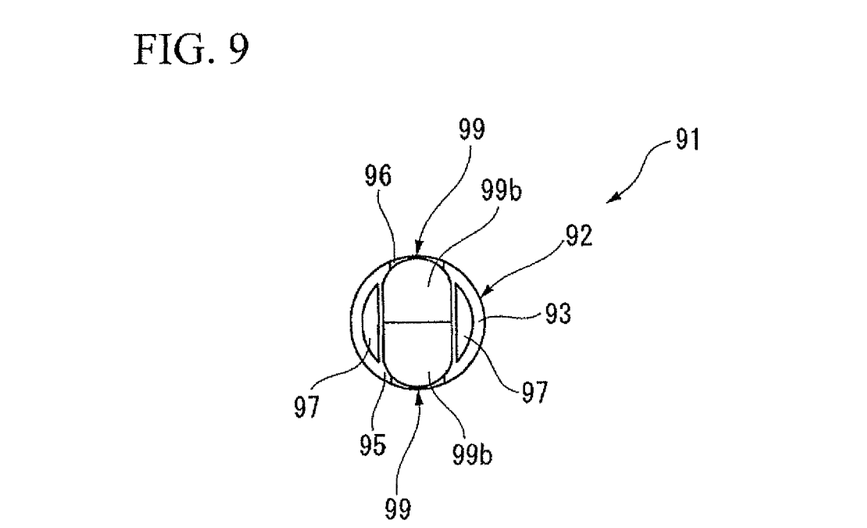
FIG. 9 is a diagram on Arrow C of FIG. 8.

As shown in FIG. 8 and FIG. 9, the biopsy forceps 91 comprise a treatment tool insertion portion 92 which is flexible and elongated. A sheath 93 of the treatment tool insertion portion 92 is hollow. The lumen of the sheath 93 forms the liquid conduit 94. To the distal end of the sheath 93 is attached an integral the open/close member support portion 95. The open/close member support portion 95 is attached crossing the diameter direction, and forms an indentation which has the slit 96. A liquid conduit 94 extends approximately in parallel to the axis line of the sheath 93. The distal end of the liquid conduit 94 branches into two liquid transport branch pipe passages which sandwich the open/close member support portion 95, and form distal end apertures 97 on the surface of the sheath 93. The two distal end apertures 97 are arranged on the outside diameter orthogonal to the lengthwise direction of the biopsy cups 99 and the open/close support member 95, and are open toward the tip (distal end). As shown in FIG. 9, the distal end apertures 97 have a shape of a circle a part of which is clipped by the open/close member support portion 95.

In the open/close member support portion 95, the pin 98 crosses the slit 96 in a direction orthogonal to the axis line of the sheath 93. By means of this pin 98, biopsy cups 99 being a set of open/close members are freely supported so as to be opened or closed in the open/close member support portion 95. The biopsy cups 99 comprise arms 99a supported by a pin 98. At the tip of the arms 99a, cups 99b protrude closer to the distal end than the sheath 93. Each cup 99b has indentation (not shown) which faces each other. The size of the set of cups 99b in the closed state is less than the outer diameter of the sheath 93. In addition, the width of the cups 99b in the direction orthogonal to the direction of opening and closing thereof is narrower than the spacing between the distal end apertures 97. The biopsy cups 99 are arranged so as to be sandwiched by the two apertures 97. To the proximal end of the arms 99a of the biopsy cups 99 are coupled operation wires 100. The operation wires 100 are pulled within a hollow the sheath 93 passing through the insertion through-hole 101 of the open/close member support portion 95, and are coupled to an un-shown treatment tool operation portion. The treatment tool operation portion is constructed so as to exclude the terminal 47 from the treatment tool operation portion 24 shown in FIG. 1.

An insertion through-hole 101 communicates to the liquid conduit 94 and the slit 96. However, the flow path area of the gap at the time when the operation wires 100 are passed through the insertion through-hole 101 is sufficiently smaller than the flow path area of the liquid transport branch pipe path 94a and the distal end aperture 97.

In performing procedures with the biopsy forceps 91, the biopsy forceps 91 are inserted into the endoscope 1 (see FIG. 1), and the biopsy cups 99 are placed in close proximity to a target site. When the target site cannot be confirmed from a hemorrhage, a physiological saline solution is injected from the lure cock 44, and is sprayed from the distal end aperture 97 through the liquid conduit 94. The physiological saline solution reaches the target site without being shielded by the biopsy cups 99, and the hemorrhage is flushed. Operating the handle 41, after opening the set of the biopsy forceps 91, the entire treatment tool insertion portion 92 is advanced, and the biopsy cups 99 are pressed against the target site. Subsequently, after closing the biopsy cups 99 and sandwiching the target site, the entire treatment tool insertion portion 92 is withdrawn to the rear, and pulled off the target site to collect it.

Since the biopsy forceps 91 have distal end apertures 97 defined in a position distant from the moving range when the biopsy cups 99 is opened or closed, the biopsy cups 99 may be opened or closed while spraying a physiological saline solution.

When hemorrhaging occurs from the site from which the target site is collected, a hemostat is injected from the lure cock 44, and is sprayed from the distal end apertures 97, reaching the hemorrhage site without being shielded by the biopsy cups 99.

According to this embodiment, liquid transport can be accomplished while the set of biopsy cups 99 are closed, and the hemorrhage can be flushed prior to treatment. Accordingly, confirmation of the target site is facilitated. Since it is possible to accomplish liquid transport while the set of biopsy cups 99 are closed, the hemostat can be dispersed after collecting the body tissue of the target site, after which hemostasis can be quickly accomplished.

By accomplishing liquid transport while the biopsy cups 99 are closed, since a large field of vision can be assured, liquid transport can be reliably realized. Since liquid transport can be accomplished when the biopsy cups 99 are opened or closed, a procedure can be quickly performed. Since the two distal end apertures 97 are defined so as to sandwich the biopsy cups 99, liquid transport can be accomplished to a broad region which includes the target site.

The amount of liquid flowing from the insertion opening 101 is made to be extremely small, with an assured amount of liquid flowing from the distal end openings 97, assuring hemostasis and the ability to flush the hemorrhage. Since the cups 99b are positioned closer to the distal end side than the distal end openings 97, a biopsy can be quickly performed. Other advantages are the same as those of the first embodiment.

Here, the treatment tool for the endoscope may be high-frequency forceps having the structure described in the third embodiment. Physiological saline solution can be transported from the distal end aperture 97 and cauterization may be performed after confirming the hemorrhage site.

Fourth Embodiment

First, an explanation is provided regarding to a fourth embodiment, with reference to FIG. 10 to FIG. 14. In the fourth embodiment, the treatment tool for the endoscope is a ligature tool on which an open/close type clip is mounted. The same symbols are applied as for those of the same elements in the first embodiment, and explanations which would be repetitive those of the first embodiment are omitted.

Figure 10:
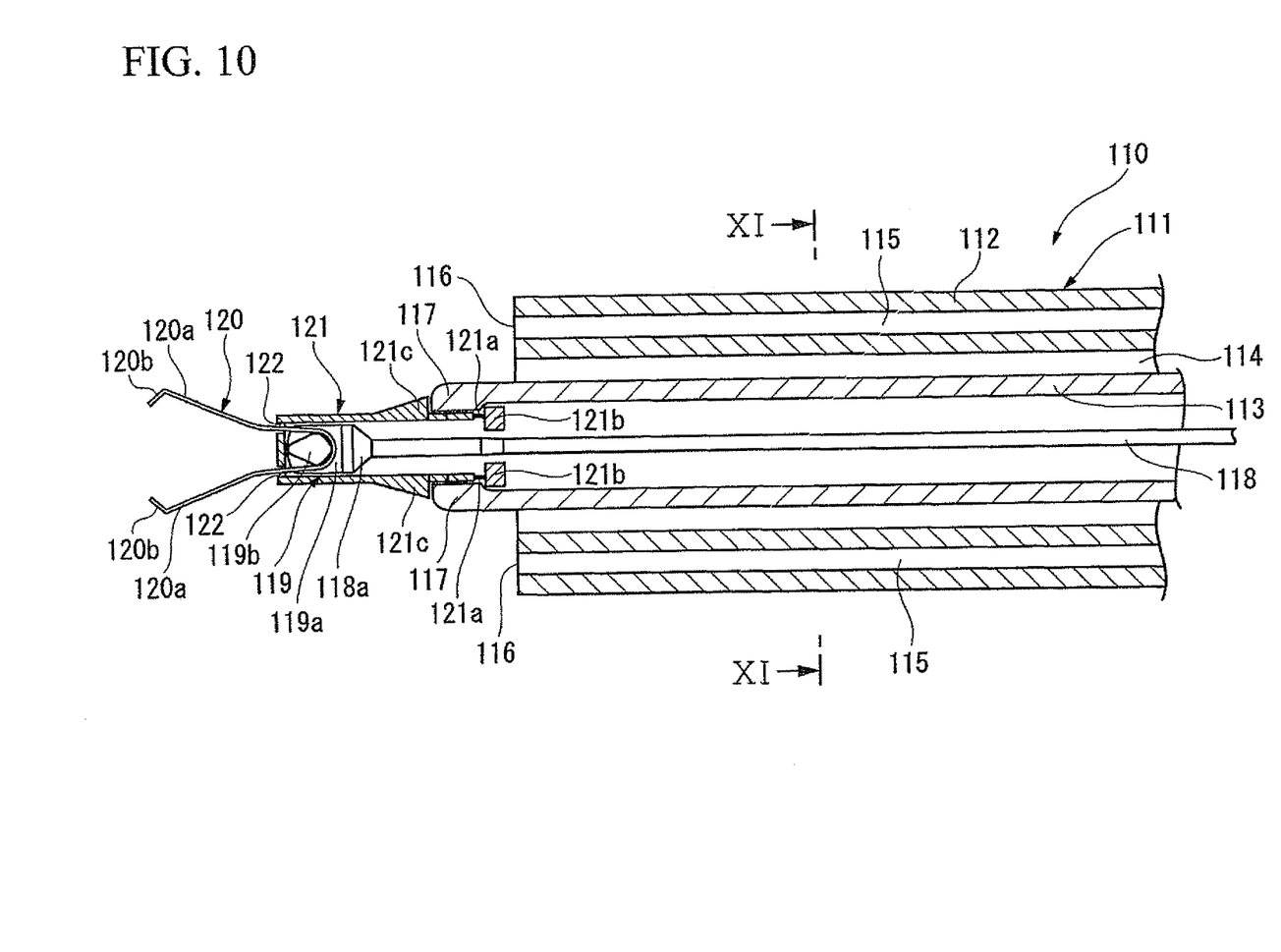
FIG. 10 is a cross-sectional view of the distal end portion of a ligature tool according to an embodiment of the present invention.
Figure 11:
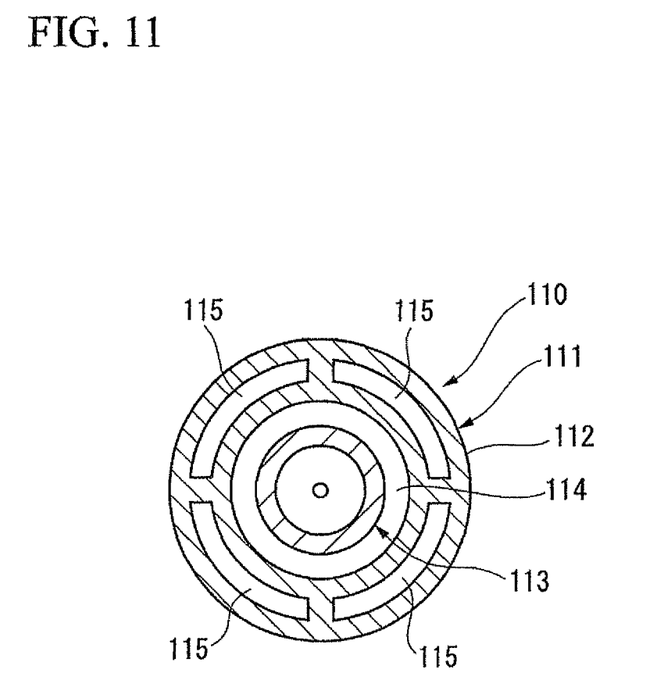
FIG. 11 is a cross-sectional view along the line XI-XI of FIG. 10.

As shown in FIG. 10, the ligature tool 110 comprises a treatment tool insertion portion 111 inserted in the treatment tool channel of the endoscope. The treatment tool insertion portion 111 comprises an external sheath 112 which is flexible and elongated, and an internal sheath 113 which can be freely inserted to or withdrawn from the external sheath 112. As shown in FIG. 11, the external sheath 112 has a hole 114, in the center of which is inserted into the internal sheath 113. In the external sheath 112, four liquid conduits 115 extend to the outer periphery of the hole 114, approximately in parallel to the axis line. Accordingly, as shown in FIG. 10, the distal end 116 of the liquid conduit 115 formed on the distal end surface of the outer sheath 112 is arranged so as to enclose hole 114.

The inner sheath 113 is formed from a tightly winded coil sheath. The periphery of the distal end aperture of the inner sheath 113 is a stopper 117 having a reduced inner diameter. An operation wire 118 is inserted so as to freely advance into or be withdrawn from within the inner sheath 113. The distal end of the operation wire 118 has an enlarge diameter part 118a, to which a connecting member 119 is attached as an integral open/close member support portion. A fragile portion 119a having a reduced thickness is formed in the distal end of connecting member 119. On the fragile side 119a, a protrusion 119b with which the clip 120 engages protrudes in a direction which is approximately orthogonal to the direction of the axis line. The connecting member 119 is housed in a cylindrical pressing member 121.

The pressing member 121 has an approximate cylindrical shape, the proximal end of which has a broader diameter following the formation of the thin fragile portion 121a. The enlarged diameter portion 121b is engageable with the proximal end side of the stopper 117 of the inner sheath 113. In addition, the distal end surface of the pressing member 121 is blocked by the two remaining slits 122. The slits 122 are formed approximately parallel to the protruding direction of the protrusion 119b of the connecting member 119. To the outside of the center of the lengthwise direction of the pressing member 121 is attached an engagement piece 121c which faces outwardly in the direction of the diameter.

To the protrusion 119b of connecting member 119 is engaged with the clip 120, which, for example, is folded around the center of a stainless steel band, and is engaged with the protrusion 119b from the proximal end side. The clip 120 comprises two clip arms 120a which extend toward the distal end. The clip arms 120a extend outwardly through each of two slits 122. The distal end of the clip arms 120a pulled out from the pressing member 121 form the nails 120b which are folded in the direction so as to come in close proximity.

To the proximal end of the inner sheath 113 is connected the operation portion, which is constructed so as to remove the terminal 47 from the treatment tool operation portion 24 shown in FIG. 1.

An explanation of an operation of an embodiment is provided next.

Figure 12:
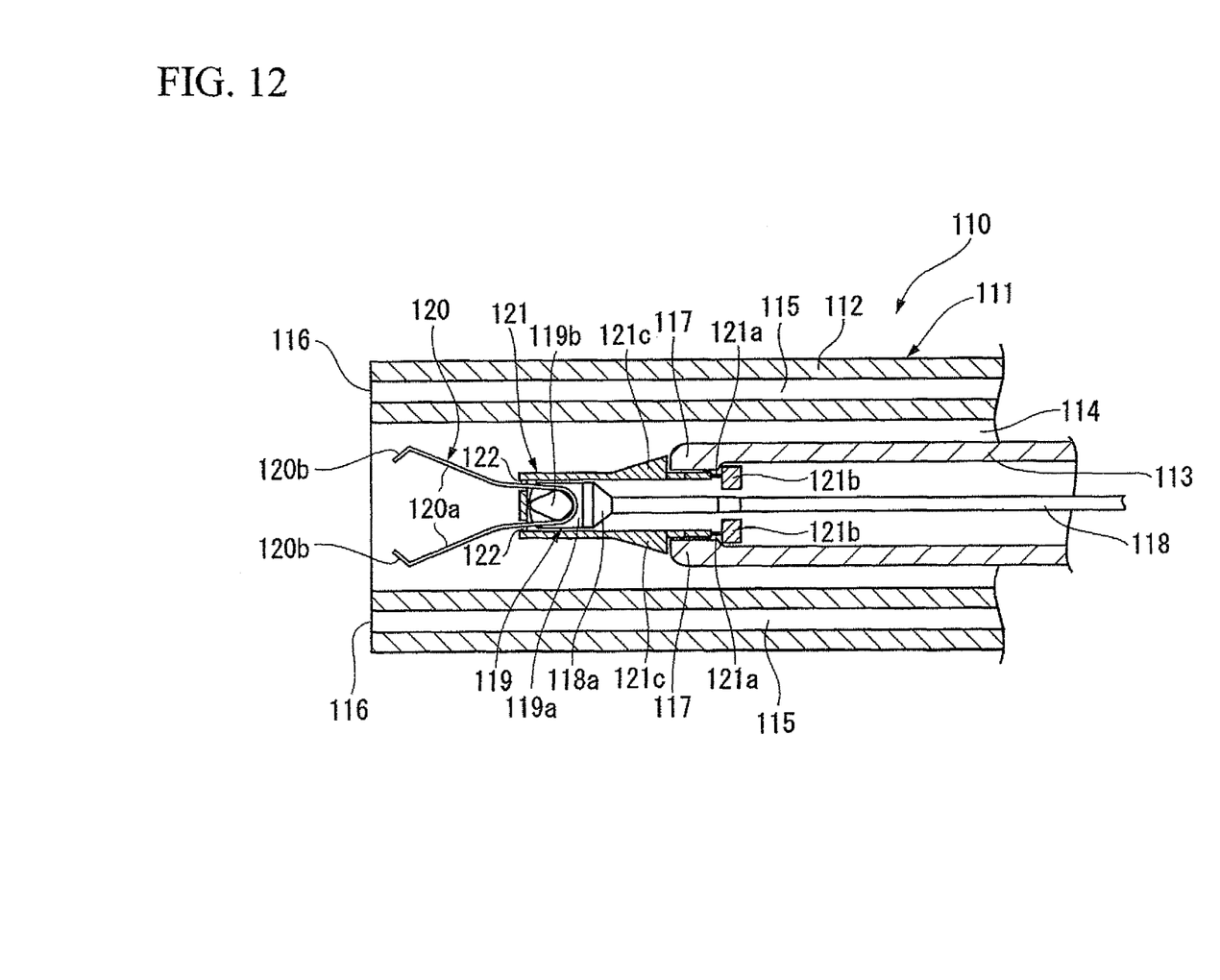
FIG. 12 is a cross-sectional view in which an internal sheath is received within an external sheath.

When accomplishing hemostasis with the clip 120, the ligature tool 10 is inserted into an endoscope. At this time, as shown in FIG. 12, the inner sheath 113 has the clip 120 which is pulled into and is received within the outer sheath 112. If the distal end of the outer sheath 112 is connected in close proximity to the target site, the inner sheath 113 is advanced relative to the outer sheath 112, and the clip 120 is made protrude from the distal end of the outer sheath 112. When the target site cannot be confirmed from a hemorrhage, physiological saline solution is injected from the lure cock 44, and is sprayed from the distal end aperture 116 through the liquid conduit 115. The physiological saline solution is sprayed from the respective four distal end apertures 116 and flushes the hemorrhage, primarily with a physiological saline solution from distal end apertures 116 which do not overlap the clip 120.

If the site of the hemorrhage is confirmed, the entire the ligature tool 110 can be pressed in, by pressing the clip 120 onto the tissue of a living body, thereby pinching the hemorrhage site with the nails. When the connecting member 119 is pulled corresponding to the pulling of the operation wire 118 after the handle 41 is pulled, the connecting member 119 is withdrawn backward and the clip 120 is returned within the pressing member 121. The clip arms 120a are closed, they sandwich a hemorrhage site, and ligature is accomplished. By pushing the handle 41 forward again to open the clip arms 120a, and ligature can be accomplished again to the hemorrhage site.

Figure 13:
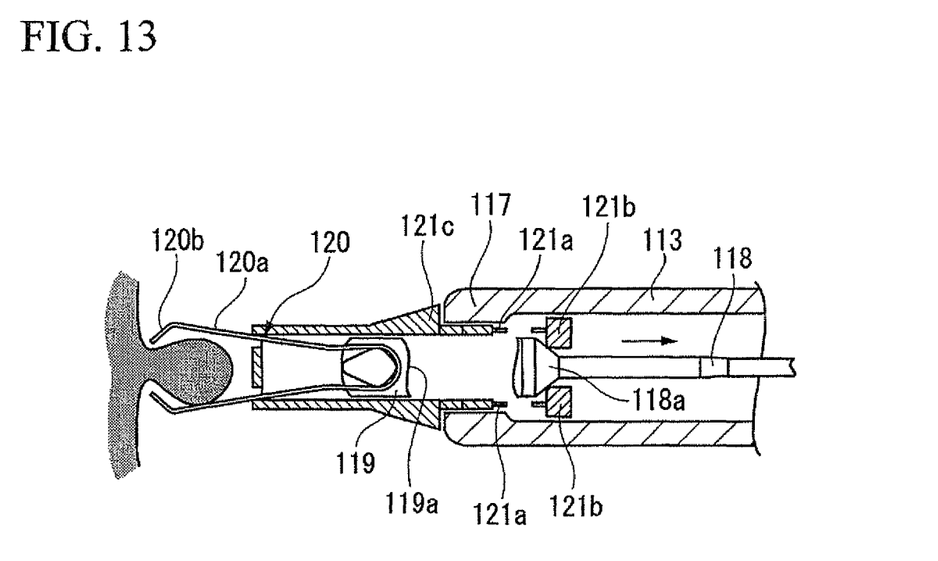
FIG. 13 is a diagram in which an engagement of a pressing member and the internal sheath is released.
Figure 14:
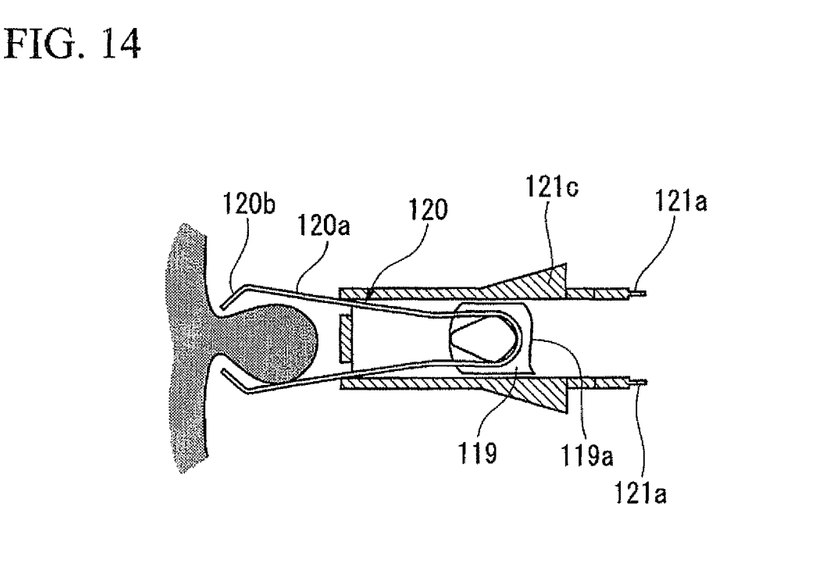
FIG. 14 is a diagram showing a clip retained within the body.

If the hemorrhage site is ligated by the clip 120, the handle 41 is strongly pulled further toward the hand, destroying the fragile portion 119a of the connecting member 119. The operation wire 118 is pulled back, and the enlarge diameter part 118a makes contact from the distal end side to the enlarged diameter portion 121b of the pressing member 121, pressing the enlarged diameter portion 121b to the proximal end side. As shown in FIG. 13, the thin fragile portion 121a is broken, and the engagement between the pressing member 121 and the inner sheath 113 is released. As shown in FIG. 14, the clip 120 which ligates the hemorrhage site and the pressing member 121 are retained within the body.

The present embodiment arranges four distal end apertures 116 of the liquid conduit 115 on the outside as the diameter direction orthogonal to the lengthwise direction of the clip 120 and the internal sheath 113, and directs the apertures toward the tip (distal end). Accordingly, liquid transport can be accomplished irrespective of the open/close state of the clip 120, making it possible to flush a hemorrhage beforehand. Accordingly, confirmation of the target site is easily accomplished. If liquid transport is accomplished until the clip 120 is closed, the field of vision can be assured to be large, guaranteeing the liquid transport. Since the distal end apertures 116 are arranged in the peripheral direction, liquid transport can be assured irrespective of the rotating position of the clip 120 or of whether the clip 120 is opened or closed. The clip may also be constructed so that the clip arms can be closed only once. However, in this embodiment, it is desirable that the clip 120 capable of being opened and closed multiple times because applying ligature to a target site is assured.

The present invention can be broadly applied without being restricted to any of the embodiments.

For example, the treatment tool for the endoscope may be provided with a nichrome line, to which direct electric current is conducted, whereby accomplishing hemostasis through the generation of heat. In addition, the treatment tool for the endoscope may be constructed so as to incise or remove a target site. Here, by spraying liquid from a liquid conduit, incision or removal may be accomplished while flushing a hemorrhage. At this time, the liquid used may include color elements.

With this treatment tool for the endoscope, when the open/close member is open, liquid transport is accomplished to the target site from the distal end aperture which is not overlapped with the open/close member. When the open/close member is closed, liquid transport is accomplished toward the target site from the distal end aperture on the periphery of the open/close member.

With the treatment tool for a endoscope, since the open/close member does not overlap the distal end aperture even if the open/close member is opened or closed, liquid transport can be accomplished irrespective of the open/close state of the open/close member.

With the treatment tool for a endoscope, since the liquid conduit is arranged outside of the treatment tool insertion portion, the structure of the device is simplified.

In the case where the treatment tool for the endoscope is high-frequency forceps, biopsy forceps, or a clip, liquid or a hemostat is transported to the liquid conduit to flush the hemorrhage.

With the treatment tool for a endoscope, since the hole required for inserting the transmission member communicates to the liquid conduit and the flow path area of the opening is small, there is only a little liquid expelled, assuring that the liquid is sprayed from the distal end aperture of the liquid conduit.

Since the present invention adopts the above-described structure, it is assured that liquid transport to the target site is accomplished corresponding to the state of use. Accordingly, hemostasis is quickly performed, enabling confirmation of the bleeding site.

INDUSTRIAL APPLICABILITY

The treatment tool for an endoscope according to the present invention is capable of being used while being inserted into a channel of an endoscope.

The invention claimed is:

1. A treatment tool for an endoscope, comprising:
 a treatment tool insertion portion to be inserted into a channel of the endoscope;
 an open/close member support portion which is provided on a distal end of the treatment tool insertion portion;
 a liquid conduit configured to transport a liquid to the open/close member support portion, an inside of the treatment tool insertion portion being the liquid conduit;
 an open/close member located in front of the liquid conduit and being supported on the open/close member support portion via a pin, the open/close member opening and closing by rotating around the pin and treating a target site; and
 a transmission member configured to transmit a driving force from a proximal end side to the open/close member, wherein
 the open/close member support portion comprises:
  a distal end aperture formed at a distal end of the open/close member support portion;
  a liquid transport lumen extending along a longitudinal direction of the open/close member support portion in front of the liquid conduit and being in fluid communication with both the distal end aperture and the liquid conduit, and
  one or more through-holes located at the open/close member support portion, the one or more through-holes being in fluid communication with the liquid conduit, the one or more through-holes being formed so as to communicate between an inside and outside of the liquid conduit at the open/close member support portion,
 the liquid transport lumen is located at a lateral side of the open/close member support portion in a radial direction,
 the transmission member extends from the proximal end side to the open/close member through the liquid conduit and through the one or more through-holes, and the transmission member is exposed to the outside of the liquid conduit distally from the one or more through-holes and is connected to the open/close member, and
 a cross-section area of the liquid transport lumen is larger than a clearance area formed between an inner surface of the one or more through-holes and an outer surface of the transmission member in a state where the transmission member is disposed in the one or more through-holes.

2. The treatment tool for the endoscope according to claim 1, wherein the distal end aperture of the liquid conduit is provided in a position which has shifted approximately 90 degrees around the axis line of the treatment tool insertion portion relative to an open/close direction of the open/close member.

3. The treatment tool for the endoscope according to claim 1, wherein the treatment tool for the endoscope is biopsy forceps, or high-frequency forceps, or a clip.

4. The treatment tool for the endoscope according to claim 1, wherein a longitudinal direction of the liquid transport lumen and an extended direction of the open/close member are parallel to each other.

5. The treatment tool for the endoscope according to claim 1, wherein a cross-section area of the liquid conduit in a direction orthogonal to a lengthwise direction of the liquid conduit is larger than the cross-section area of the liquid transport lumen.

* * * * *